United States Patent [19]

Newton et al.

[11] Patent Number: 5,098,695

[45] Date of Patent: Mar. 24, 1992

[54] PRECIPITATED SILICAS

[75] Inventors: John R. Newton, Cheshire; James P. Quinn, Birkenhead; Peter W. Stanier, Cheshire, all of England

[73] Assignee: Unilever Patent Holdings, B.V., Rotterdam, Netherlands

[21] Appl. No.: 645,301

[22] Filed: Jan. 24, 1991

Related U.S. Application Data

[63] Continuation of Ser. No. 376,921, Jul. 10, 1989, abandoned, which is a continuation of Ser. No. 937,498, Dec. 3, 1986, abandoned.

[30] Foreign Application Priority Data

Dec. 3, 1985 [GB] United Kingdom ................. 8529796

[51] Int. Cl.$^5$ ...................... A61K 7/16; C01B 33/142; C01B 33/154
[52] U.S. Cl. ..................................... 424/49; 423/335; 423/339
[58] Field of Search ................... 424/49; 423/335, 339

[56] References Cited

U.S. PATENT DOCUMENTS

| | | | |
|---|---|---|---|
| 3,864,470 | 2/1975 | Watson | 424/49 |
| 4,045,240 | 8/1977 | Wason et al. | 423/339 |
| 4,105,757 | 8/1978 | Wason | 424/49 |
| 4,122,160 | 10/1978 | Wason | 424/49 |
| 4,191,742 | 3/1980 | Wason | 424/49 |
| 4,243,428 | 1/1981 | Donnet et al. | 423/339 |
| 4,857,289 | 8/1989 | Naurouth | 423/339 |

FOREIGN PATENT DOCUMENTS

| | | |
|---|---|---|
| 1190964 | 5/1970 | United Kingdom . |
| 1264292 | 2/1972 | United Kingdom . |
| 1350659 | 4/1974 | United Kingdom . |
| 1482354 | 8/1977 | United Kingdom . |
| 1482355 | 8/1977 | United Kingdom . |
| 1501905 | 2/1978 | United Kingdom . |
| 2038303 | 7/1980 | United Kingdom . |
| 2146317 | 9/1984 | United Kingdom . |
| 2146318 | 9/1984 | United Kingdom . |
| 2151922 | 7/1985 | United Kingdom . |

Primary Examiner—Ronald W. Griffin
Attorney, Agent, or Firm—Cushman, Darby & Cushman

[57] ABSTRACT

A precipitated silica, suitable for use in toothpastes, has a high absorbency, i.e. 110 to 180 cm$^3$100 g, and good abrasivity with a plastics abrasion value of 12 to 20. The silica provides abrasion even at a relatively low particle size.

2 Claims, No Drawings

PRECIPITATED SILICAS

This is a continuation of application Ser. No. 07/376,921, filed on July 10, 1989, which was abandoned upon the filing hereof which is a continuation of Ser. No. 06/937,498 filed Dec. 3, 1986, both now abandoned.

FIELD OF THE INVENTION

This invention relates to synthetic precipitated silicas of use, for example, as abrasive agents in toothpaste compositions.

BACKGROUND TO THE INVENTION

Toothpaste compositions are well characterised in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients. Of these components the abrasive agent is required to provide the appropriate cleaning and plaque removal without subjecting the tooth itself to excessive abrasion. Typically a toothpaste composition will contain from about 5% to about 50%, preferably up to about 30%, by weight of abrasive. Commonly used abrasives are aluminas, calcium carbonates and calcium phosphates. More recently synthetic silicas have been adopted because of their efficient cleaning, compatibility with other ingredients and their physical properties.

Normally, silicas used as abrasives in toothpaste formulations have low structure as defined by their oil absorption. In general, silicas with oil absorptions less than 110 cm$^3$/100 g are considered to have low structure, whereas those in excess of 180 cm$^3$/100 g have high structure and they are usually employed as thickeners, fillers and liquid carriers.

Examples of abrasive silicas with low structure can be found in UK 1;482,354; 1,482,355 (Huber) and UK 1,264,292 (Unilever). In terms of abrasivity, the silicas disclosed in the Huber specifications would be defined as medium, whereas those described in the Unilever patent are considered high.

Medium structured silicas in the oil absorption range 110-180 cm$^3$/100 g have low levels of abrasivity and are normally used as structuring and polishing agents in toothpaste formulations. Examples are U.S. Pat. No. 3,864,470 (Unilever) where the product Neosyl ® (typical oil absorption value 160 cm$^3$/100 g) is referred to as a polishing agent any UK 1501905 in which Huber describe a polishing silica with medium structure.

GENERAL DESCRIPTION OF THE INVENTION

The precipitated silicas of the invention have remarkably high structure, as defined by oil absorption, in view of the level of abrasion they can supply within the stated particle size range. Normally silicas which are capable of abrading surfaces have low structure i.e. low oil absorption.

The high values of oil absorption can be expected to give more structure (liquid thickening effect) to formulations containing the precipitated silica abrasives of the invention.

The invention provides an amorphous precipitated silica having i) a surface area in the range from about 10, preferably from about 100, to about 400m$^2$/g, usually about 250 to about 350 m$^2$/g, ii) an oil absorption (using linseed oil) of about 110 to about 180cm$^3$/100 g, preferably at least 120 cm$^3$/g, iii) a weight mean particle size in the range 3 microns to 20 microns, preferably above 5 micron and below 15 microns, and iv) a perspex abrasion value in the range from about 12 to about 20, these latter values correspond to Radioactive Dentine Abrasion values of 60 to 165.

The precipitated silicas of the invention are capable of providing satisfactory abrasion even at relatively low particle sizes i.e. 3 to 7 micron range. Abrasive materials can also be obtained at particle sizes beyond the stated upper limit but they are not suitable for use in toothpastes because of the unacceptable mouth feel of the coarser particles.

The percentage transmission (589nm) of the silicas of the invention is at least 60% in the range of refractive index 1.438 and 1.448 and at least 70% in the range 1.440 to 1.445. These transmissions show the silicas of the invention are of value for opaque and translucent dentifrices but not the commercially used transparent formulations.

The invention extends to a method of reacting a silicate solution and acid solution inn the presence of electrolyte to provide precipitated silicas according to the invention.

Standard Procedures

The silicas of the invention are defined in terms of their physical and chemical properties. The standard test methods used to determine these properties are:

Surface Area

Surface area is determined by standard nitrogen adsorption methods of Brunauer, Emmett and Teller (BET) using a single point method with a Sorpty 1750 apparatus supplied by Carlo Erba company of Italy. The sample was outgassed under vacuum at 270° C. for 1 hour before measurement.

ii) Oil Absorption

The oil absorption is determined by the ASTM spatula rub-out method (American Society of Test Material Standards D, 281).

The test is based upon the principle of mixing linseed oil with a silica by rubbing with a spatula on a smooth surface until a stiff putty-like paste is formed which will not break or separate when it is cut with the spatula. The volume of oil used is then put into the following equation:

$$\text{Oil absorption} = \frac{\text{cm}^3 \text{ oil absorption} \times 100}{\text{wt. of silica sample in gms}}$$

$$= \text{cm}^3 \text{ oil/100 g silica}$$

iii) Weight Mean Particle Size

The weight mean particle size of the silicas was determined with the aid of a Malvern Particlesizer, Model 3600 E. This instrument, made by Malvern Instruments, Malvern, Worcestershire uses the principle of Fraunhöffer diffraction utilising a low power He/Ne laser. Before measurement the sample was dispersed ultrasonically in water for a period of 7 minutes to form an aqueous suspension.

iv) Perspex Abrasion Value

This test is based upon a toothbrush head brushing a perspex plate in contact with a suspension of the silica in a sorbitol/glycerol mixture. Normally the slurry composition is as follows:

| | |
|---|---|
| Silica | 2.5 grams |
| Glycerol | 10.0 grams |
| Sorbitol | 23.0 grams |

All components are weighed into a beaker and dispersed for 2 minutes at 1500 rpm using a simple stirrer. A 110mm×55mm×3mm sheet of standard clear Perspex is used for the test, supplied by Imperial Chemical Industries PLC of England under code 000.

The test is carried out using a modified Wet Paint Scrub Tester produced by Research Equipment Limited, Wellington Road, Hampton Hill, Middlesex. The modification is to change the holder so that a toothbrush can be used instead of a paint brush. In addition a weight of 14 ozs (398g) is attached to the brush to force the brush onto the perspex plate.

A Galvanometer is calibrated using a 45° Plaspec gloss head detector and a standard (50% gloss) reflecting plate. The Galvanometer reading is adjusted to a value of 50 under these conditions. The reading of the fresh perspex plate is then carried out using the same reflectance arrangement.

The fresh piece of perspex is then fitted into a holder. Two mls of the dispersed silica, sufficient to lubricate fully the brushing stroke, is placed on the plate and the brush head lowered onto the plate. The machine is switched on and the plate subjected to three hundred strokes of the weighted brush head. The plate is removed from the holder and all the suspension is washed off. It is then dried and re-measured for its gloss value. The abrasion value is the difference between the unabraded value and the value after abrasion.

This test procedure, when applied to known abrasives, gave the following values:

| | Perspex abrasion value |
|---|---|
| Calcium carbonate (15 micron) | 32 |
| Silica xerogel (10 micron) prepared by UK 1264292 method | 25 |
| Alumina trihydrate (Gibbsite) 15 micron | 16 |
| Calcium pyrophosphate (10 micron) | 14 |
| Dicalcium phosphate dihydrate (15 micron) | 7 |
| Neosyl ® as used in US 3864470 (15 micron) | 8 | v) Loose Bulk Density

Loose bulk density is determined by weighing approximately 180 ml of silica into a dry 250 ml measuring cylinder, inverting the cylinder ten times to remove air pockets and reading the final settled volume.

$$\text{Loose bulk density} = \frac{\text{Weight}}{\text{Volume}} \times 1000 \text{ g/l}$$

vi) Electrolyte Levels

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

vii) Moisture Loss at 105° C.

Moisture loss is determined by the loss in weight of a silica when dried to constant weight in an electric oven at 105° C.

viii) Ignition Loss at 1000° C.

Ignition loss is determined by the loss in weight of a silica when ignited in a furnace at 1000° C. to constant weight.

ix) pH

This measurement is carried out on a 5% w/w suspension of the silica in boiled demineralised water ($CO_2$ free).

x) Filter Cake Ignition Loss

Filter cake ignition loss is determined by the loss in weight of a silica filter cake when ignited in a furnace at 1000° C. to constant weight.

xi) Radioactive Dentine Abrasion Test (RDA):

The procedure follows the method for assessment of dentifrice abrasivity recommended by the American Dental Association (Journal of Dental Research 55 (4) 563, 1976). In this procedure extracted human teeth are irradiated with a neutron flux and subjected to a standard brushing regime. The radioactive phosphorous 32 removed from the dentin in the roots is used as the index of the abrasion of the dentifrice tested. A reference slurry containing 10 g of calcium pyrophosphate in 15 ml of 0.5% aqueous solution of sodium carboxymethyl cellulose is also measured and the RDA of this mixture is arbitrarily taken as 100. The precipitated silica to be tested is prepared as a suspension at the same concentration as the pyrophosphate and submitted to the same brushing regime.

The RDA's obtained are quoted for a number of the examples of silicas prepared within the present invention. By examining a range of silicas, including those described in the present invention, it has been found there is a correlation between plastics abrasion value and RDA over fifteen samples with a correlation coefficient of 0.91 (confidence 99%).

xii) Refractive index (RI)/transmission

A sample silica was dispersed in a range of water/sorbitol (70% syrup) mixtures. The RI for each dispersion was measured together with the percentage transmission using illumination of 589 nm and water as a blank. The RI of the silica corresponds to maximum transmission and presentation of the transmission against RI graphically allows the transmission over a range of RI to be readily demonstrated.

xiii) Viscosity determination

Slurries of silica, at 10% and 20% w/w concentration, in 70% Sorbitol Syrup (E420) are prepared using a Heidolph stirrer at 1500 rpm for 10 minutes.

The viscosity of the slurry is determined @100s$^{-1}$ shear rate using a Haake Rotovisco ®RV22 @ 25° C.

The following conditions are used:
Measuring head M500
Sensor system MVI
PG 142 Programme 1-3-1
Speed range 0–128 rpm

SPECIFIC DESCRIPTION OF THE INVENTION

Examples of the preparation of precipitated silicas will now be given to illustrate but not limit the invention.

A heated stirred reaction vessel was used for the silicate/acid reaction.

The solutions used in the process were as follows:

i) Sodium silicate solutions having a $SiO_2:Na_2O$ ratio in the range of 1.9 to 3.4:1.

ii) A sulphuric acid solution of specific gravity 1.11 ( 16.1% W/W solution) to 1.185 (25.9% W/W solution).

iii) An electrolyte solution as defined in each example.

The following procedure was adopted in the preparation of the precipitated silicas. Values of reactant concentrations and volumes, and reaction temperatures are given in Table 1.

(A) liters of water were placed in the vessel together with (B) liters of electrolyte solution and (C) liters of the sodium silicate solution. This mixture was then stirred and heated to (E)° C.

The sodium silicate ((D) liters) and sulphuric acid ((F) liters) solutions were then added simultaneously over a period of about 20 minutes with stirring while maintaining the temperature at (E)° C. The flow rates of the silicate and acid solutions were uniform throughout the addition period to ensure that a constant pH was maintained in the vessel. Sulphuric acid solution was then added over a period of 10 minutes with continued mixing to reduce the pH of the liquid to the range of 3.0 to 3.5. During this addition of acid the temperature was maintained. Optionally a hydrothermal ageing step can be introduced during the acid addition if materials with lower surface areas are required (this is illustrated by Example 10). The resultant slurry was then filtered and washed with water to remove excess electrolyte. Typically, for a toothpaste application, the residual electrolyte would be less than 2% on a dry weight basis.

After washing, the filter cake, which had a moisture content of (G)%, was flash dried and comminuted to the desired particle size range.

During addition of volume F in Example 10 the addition was stopped when the pH reached 8.5. The medium was then held at this pH and 98° C. for 90 minutes before the remainder of the acid was added.

The precipitated silica obtained had the properties, expressed on a dry weight basis, as listed in Table II.

In Table III the thickening capability of precipitated silicas of this invention are compared with commercially available silicas of differing structure as defined by oil absorption. Clearly, the silicas as incorporated give rise to a higher level of thickening than that usually associated with an abrasive as shown by the viscosity values obtained at the different loadings of silica in sorbitol syrup.

The precipitated silicas prepared as described provided satisfactory cleaning properties for the toothpastes in which they were incorporated. The toothpastes had commercially suitable properties for stability and usage. Typical formulations using the silicas of this invention ar listed below.

| Opaque, White Toothpaste | | Translucent Gel Toothpaste | |
|---|---|---|---|
| | % | | % |
| Sorbosil TC10 | 11.0 | Sorbosil TC10 | 6.0 |
| Silica of invention | 9.5 | Silica of invention | 16.0 |
| Xanthan Gum | 1.1 | Sodium Carboxymethyl Cellulose | 0.7 |
| Sorbitol, 70% non-crystallisable | 52.0 | Sorbitol, 70% non-crystallisable | 60.0 |
| Sodium Lauryl Sulphate | 1.5 | Polyethylene Glycol 1500 | 5.0 |
| Sodium Monofluoro-phosphate | 0.8 | Sodium Lauryl Sulphate | 1.5 |
| Flavour | 1.0 | Sodium Monofluoro-phosphate | 0.8 |
| Saccharin | 0.2 | Flavour | 1.0 |
| Titanium Dioxide | 1.0 | Saacharin | 0.2 |
| Water & minor ingredients to | 100 | Colour, Blue, CI42090 | 0.002 |
| | | Water & minor ingredients to | 100 |
| Properties - Initial | | Properties - Initial | |
| Density gml$^{-1}$ (25° C.) | 1.3 | Density gml$^{-1}$ (25° C.) | 1.37 |
| RDA | 85 | RDA | 109 |

Sorbosil TC10 is a thickening silica obtainable from Crosfield Chemicals of Warrington, England.

TABLE I

| Example No. | 1 | 2 | 3 | 4 | 5 | 6 | 7 | 8 | 9 | 10 |
|---|---|---|---|---|---|---|---|---|---|---|
| Vessel capacity (liters) | 325 | 325 | 64 | 325 | 64 | 325 | 64 | 325 | 64 | 64 |
| Water volume (A) (liters) | 87 | 87 | 19.4 | 101 | 18.2 | 116 | 20.9 | 87 | 22.1 | 21.7 |
| Electrolyte used | NaCl | NaCl | NaCl | NaCl | NaCl | NaCl | NaCl | NaCl | Na$_2$CO$_3$ | NaCl |
| Concn. of electrolyte (% w/w) | 25 | 25 | 25 | 25 | 25 | 25 | 25 | 25 | 21.3 | 25.0 |
| Vol. of electrolyte (B) (liters) | 7.6 | 7.6 | 1.44 | 9.5 | 1.44 | 7 | 1.33 | 6.66 | 3.3 | 1.67 |
| Silicate ratio SiO$_2$/Na$_2$O by weight | 3.37 | 3.37 | 3.33 | 3.29 | 3.33 | 3.28 | 1.9 | 3.37 | 3.31 | 3.37 |
| SiO$_2$ Concentration in sodium silicate (% w/w) | 16.4 | 16.4 | 16.4 | 16.4 | 16.4 | 16.9 | 15.7 | 16.4 | 16.6 | 16.4 |
| Silicate volume (C) (liters) | 0.8 | 0.8 | 0.2 | 1 | 0.2 | 1 | 0.2 | 0.8 | 0.2 | 0.2 |
| Silicate volume (D) (liters) | 82 | 82 | 22 | 113.5 | 22 | 101 | 20.0 | 82 | 20.0 | 20.2 |
| Acid concentration (% w/w) | 16.8 | 16.8 | 16.5 | 17.4 | 16.5 | 16.8 | 24.6 | 16.8 | 17.4 | 17.2 |
| Acid volume (F) (liters) | 31.5 | 31.5 | 8.6 | 44.0 | 9.8 | 42 | 8.9 | 31.5 | 7.8 | 7.9 |
| Temperature °C. (E) | 98 | 98 | 98 | 98 | 90 | 98 | 98 | 98 | 98 | 98 |

TABLE 2

| Example No. | 1 | 2 | 3 | 4 | 5 | 6 | 7 | 8 | 9 | 10 |
|---|---|---|---|---|---|---|---|---|---|---|
| Cake ignition loss @ 1000° C. % W/W (G) | 65.3 | 65.3 | 49.7 | 56.3 | 59.2 | 61.5 | 57.1 | 63.4 | 70.8 | 50.0 |
| Surface area (m$^2$g$^{-1}$) | 310 | 310 | 287 | 311 | 341 | 278 | 353 | 270 | 260 | 20 |
| Oil absorption (cm$^3$/100 g) | 145 | 115 | 120 | 115 | 160 | 170 | 135 | 177 | 170 | 140 |
| Weight mean particle size (micron) | 7.2 | 4.2 | 12.0 | 9.3 | 15.3 | 10.0 | 12.5 | 7.6 | 19.3 | 12.0 |
| Plastic abrasion value | 18 | 14 | 14 | 14 | 18 | 12 | 15 | 14 | 14 | 14 |
| RDA | 125 | 137 | NM | 111 | NM | 71 | NM | 83 | NM | NM |
| Loose bulk density | 230 | 180 | 120 | 189 | 155 | 203 | 135 | 187 | 245 | 150 |

TABLE 2-continued

| Example No. | 1 | 2 | 3 | 4 | 5 | 6 | 7 | 8 | 9 | 10 |
|---|---|---|---|---|---|---|---|---|---|---|
| (g·l⁻¹) | | | | | | | | | | |

NM = not measured

TABLE III

Viscosity of silicas dispersed in
70% Sorbitol Syrup (E420)
mPas at 100s⁻¹

|  | 10% w/w Silica | 20% w/w Silica |
|---|---|---|
| Example 1 Silica | 211 | 713 |
| Example 8 Silica | 335 | 2146 |
| Medium Structure commercially available silica (Neosyl ®) | 290 | 1406 |
| Low Structure commercially available silica abrasive | 186 | 303 |
| High Structure commercially available silica | 1448 | Too high to measure on this sensor. |

We claim:

1. An amorphous precipitated silica having
   i) a surface area in the range from about 250 to about 350 m²/g,
   ii) an oil absorption (using linseed oil) of about 120 to about 180 cm³/100 g,
   iii) a weight mean particle size in the range from about 5 to about 15 microns and
   iv) a perspex abrasion value in the range from about 12 to about 20.

2. A composition containing toothpaste and from about 5% to about 50% by weight, of an amorphous precipitated silica defined in claim 1.

* * * * *